United States Patent
Wolff

(10) Patent No.: US 12,023,257 B2
(45) Date of Patent: Jul. 2, 2024

(54) MESH SPACER HYBRID SPINAL IMPLANT

(71) Applicant: Spineology Inc., St. Paul, MN (US)

(72) Inventor: Kyle Wolff, St. Paul Park, MN (US)

(73) Assignee: Spineology Inc., St. Paul, MN (US)

( * ) Notice: Subject to any disclaimer, the term of this patent is extended or adjusted under 35 U.S.C. 154(b) by 0 days.

(21) Appl. No.: 17/960,801

(22) Filed: Oct. 5, 2022

(65) Prior Publication Data

US 2023/0105717 A1 Apr. 6, 2023

Related U.S. Application Data

(60) Provisional application No. 63/252,337, filed on Oct. 5, 2021.

(51) Int. Cl.
*A61F 2/44* (2006.01)
*A61F 2/30* (2006.01)

(52) U.S. Cl.
CPC ............ *A61F 2/4455* (2013.01); *A61F 2/441* (2013.01); *A61F 2002/30019* (2013.01); *A61F 2002/30354* (2013.01); *A61F 2002/30784* (2013.01); *A61F 2002/448* (2013.01); *A61F 2310/00023* (2013.01)

(58) Field of Classification Search
CPC ............ A61F 2310/00023; A61F 2/441; A61F 2/442; A61F 2/4425; A61F 2/4455; A61F 2/4465; A61F 2/447; A61F 2/448; A61F 2002/443; A61F 2002/4435; A61F 2002/4485

USPC ............................................ 623/17.11–17.16
See application file for complete search history.

(56) References Cited

U.S. PATENT DOCUMENTS

| | | |
|---|---|---|
| 4,961,740 A | 10/1990 | Ray et al. |
| 6,039,761 A | 3/2000 | Li et al. |
| 7,534,268 B2 | 5/2009 | Hudgins et al. |
| 9,198,765 B1 | 12/2015 | Pimenta |
| 9,687,356 B1* | 6/2017 | Spangler ............... A61F 2/4611 |
| 9,730,803 B2 | 8/2017 | DiMauro et al. |
| 9,844,444 B2 | 12/2017 | Wolfe et al. |
| 9,925,058 B2 | 3/2018 | Wolfe et al. |
| 2002/0099444 A1 | 7/2002 | Boyd et al. |
| 2003/0009222 A1 | 1/2003 | Fruh et al. |
| 2005/0113919 A1* | 5/2005 | Cragg .................... A61F 2/442 |
| | | 623/17.11 |
| 2005/0113924 A1 | 5/2005 | Buttermann |
| 2005/0197702 A1 | 9/2005 | Coppes et al. |
| 2006/0155297 A1 | 7/2006 | Ainsworth et al. |
| 2007/0067036 A1 | 3/2007 | Hudgins et al. |
| 2007/0260314 A1 | 11/2007 | Biyani |

(Continued)

*Primary Examiner* — Eduardo C Robert
*Assistant Examiner* — Christina NegrelliRodriguez
(74) *Attorney, Agent, or Firm* — Skaar Ulbrich Macari, P.A.

(57) ABSTRACT

A hybrid spinal implant for performing an intervertebral fusion procedure can include a pair of spacers separated by an expandable container that are formed of a porous titanium scaffold material. A connecting rod can span longitudinally between the pair of spacers. The spacers can be formed of titanium or PEEK, with endplates that are formed of the porous titanium scaffold material. The endplates can be bioactive. Exposed surfaces of the porous titanium scaffold material can be coated in a snag-preventing substance. The expandable container can be formed of a mesh material.

19 Claims, 2 Drawing Sheets

(56) References Cited

U.S. PATENT DOCUMENTS

2009/0112323 A1 4/2009 Hestad et al.
2012/0022652 A1 1/2012 Berger et al.

* cited by examiner

MESH SPACER HYBRID SPINAL IMPLANT

PRIORITY

This application claims the benefit of U.S. Provisional Application Ser. No. 63/252,337, filed on Oct. 5, 2021, which is hereby incorporated herein by reference in its entirety.

FIELD

The present invention generally relates to a spacer/mesh container hybrid implant for use in the spine.

BACKGROUND

PEEK spacers are commonly used in spine surgery, particularly fusion surgery. Often bone graft or other fill material is used with a spacer to help promote bony fusion. It is desirable that the fill material contacts the vertebral endplates while the spacer provides structural support. In an attempt to minimize the size of spacers, traditional PEEK spacers lack adequate cavities for fill material insertion. As such, fill material is often packed around the spacer, rather than in the spacer. Uncontained fill material does pose a risk of migrating to surrounding anatomy which can lead to patient injury.

It is desirable to have a spacer small enough to be inserted via a minimally invasive or even percutaneous approach, while allowing for greater fill material containment and fill material contact with the vertebral endplates. There is a continuing need for a spacer that is small enough to fit through an MIS or percutaneous approach, yet able to expand upon insertion to fully support and/or stabilize the intervertebral space while containing fill material therewithin.

SUMMARY

A hybrid spinal implant for performing an intervertebral fusion procedure can include a pair of spacers separated by an expandable container that are formed of a porous titanium scaffold material (e.g., Osteosync Ti). A connecting rod can span longitudinally between the pair of spacers. The spacers can be formed of titanium (e.g., Ti-6Al-4V Titanium) or PEEK, with endplates that are formed of the porous titanium scaffold material. The endplates can be bioactive. Exposed surfaces of the porous titanium scaffold material can be coated in a snag-preventing substance. The expandable container can be formed of a mesh material.

In one example, a hybrid spinal implant for performing an intervertebral fusion on adjacent vertebral bodies in a patient, and for being located in a space between opposing end plates of the adjacent vertebral bodies can include a first spacer, a second spacer, a connecting rod spanning longitudinally between the first spacer and the second spacer, and a porous and expandable enclosed container disposed longitudinally between the first spacer and the second spacer. The connecting rod can pass through the expandable enclosed container in a direction parallel to the opposing end plates of the adjacent vertebral bodies when the hybrid spinal implant is located in the space between opposing end plates of adjacent vertebral bodies. Each of the first spacer and the second spacer can comprise a porous titanium scaffold material.

Each of the first spacer and the second spacer can be formed of titanium with endplates that are formed of the porous titanium scaffold material for contacting the opposing end plates of the adjacent vertebral bodies. Each of the first spacer and the second spacer also can comprise a porous titanium scaffold material and PEEK. Each of the first spacer and the second spacer can comprise bioactive endplates for contacting the opposing end plates of the adjacent vertebral bodies. One or more exposed surfaces of the porous titanium scaffold material can be coated in a snag-preventing substance.

The porous and expandable enclosed container can be exposed between the first spacer and the second spacer to the opposing end plates when the implant is implanted in the space between opposing end plates.

A longitudinal end of the connecting rod can be secured to the first spacer via a threaded fastener that is threaded into the first spacer sufficiently to engage a detent or recess defined in the connecting rod.

The porous and expandable enclosed container can comprise a mesh material.

At least one of the top and bottom surfaces of the first spacer can comprise a textured surface for engaging a respective opposing end plate of the adjacent vertebral bodies.

Each of the first and second spacers can define a non-circular outer perimeter in a cross-section taken perpendicular to their longitudinal axis.

In another example, a method of placing an implant for intervertebral fusion between adjacent vertebral bodies in a patient, can include forming the first and second spacers from a porous titanium scaffold material, inserting the hybrid spinal implant in a space between the adjacent vertebral bodies so that the implant is oriented such that respective opposing surfaces of the first spacer and the second spacer respectively contacts both of the adjacent vertebral bodies simultaneously, and, without altering the height dimension of the first spacer, filling the expandable container with fill material such that the expandable container expands to mutually contact both of the adjacent vertebral bodies. The expandable container can comprise a mesh material and be porous.

The step of forming the first and second spacers from a porous titanium scaffold material can include forming the first spacer and the second spacer of titanium with endplates that are formed of the porous titanium scaffold material. The step of forming the first and second spacers from a porous titanium scaffold material can further include forming the first spacer and the second spacer of PEEK. One or more exposed surfaces of the porous titanium scaffold material can be coated with a snag-preventing substance.

A connecting rod can be placed between the first and second spacers and also pass through the expandable container. A longitudinal end of the connecting rod can be secured to the first spacer with a fastener threaded into the first spacer sufficiently to engage a detent or recess defined in the connecting rod.

The step of inserting the implant in a space between the adjacent vertebral bodies can be performed via minimally invasive surgical (MIS) techniques and/or percutaneous surgical techniques. The implant can be inserted between the adjacent vertebral bodies in a direction parallel to respective opposing end plates of the adjacent vertebral bodies.

The detailed technology and preferred embodiments implemented for the subject invention are described in the following paragraphs accompanying the appended drawings for people skilled in this field to well appreciate the features of the claimed invention. It is understood that the features mentioned hereinbefore and those to be commented on hereinafter may be used not only in the specified combinations, but also in other combinations or in isolation, without departing from the scope of the present invention.

Figure 1:
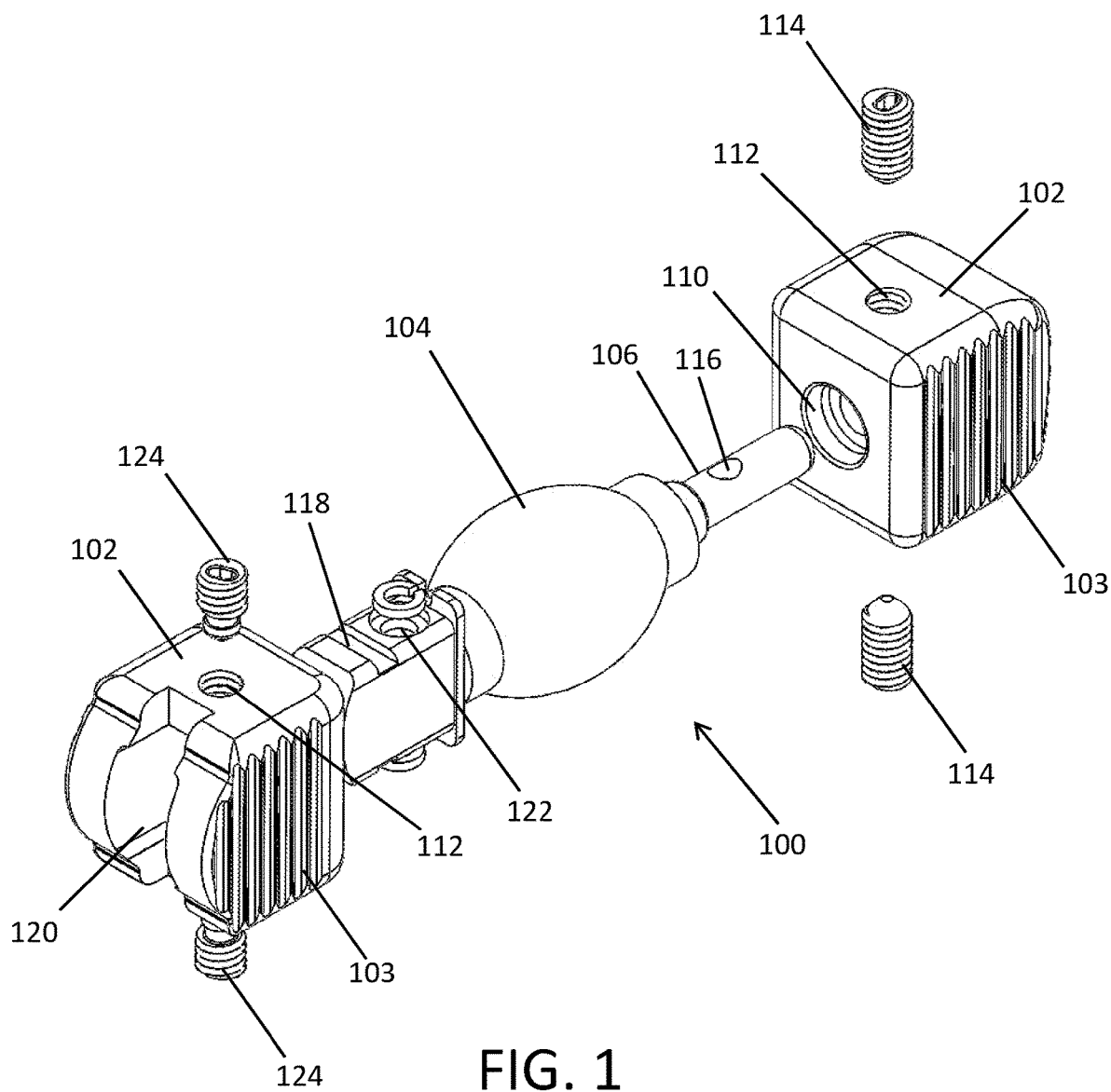
FIG. 1 depicts a perspective view of a mesh spacer hybrid spinal implant according to an embodiment of the present invention.

While the invention is amenable to various modifications and alternative forms, specifics thereof have been shown by way of example in the drawings and will be described in detail. It should be understood, however, that the intention is not to limit the invention to the particular example embodiments described. On the contrary, the invention is to cover all modifications, equivalents, and alternatives falling within the spirit and scope of the invention as defined by the appended claims. For illustrative purposes, cross-hatching, dashing or shading in the figures is provided to demonstrate sealed portions and/or integrated regions or devices for the package.

DETAILED DESCRIPTION

In the following descriptions, the present invention will be explained with reference to example embodiments thereof. However, these embodiments are not intended to limit the present invention to any specific example, embodiment, environment, applications or particular implementations described in these embodiments. Therefore, description of these embodiments is only for purpose of illustration rather than to limit the present invention. It should be appreciated that, in the following embodiments and the attached drawings, elements unrelated to the present invention are omitted from depiction; and dimensional relationships among individual elements in the attached drawings are illustrated only for ease of understanding, but not to limit the actual scale.

Figure 2:
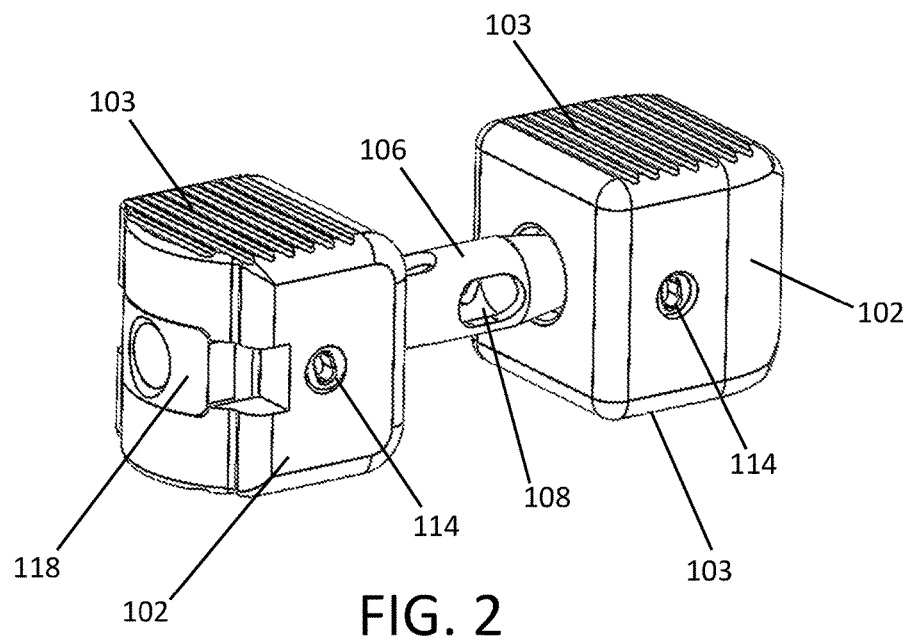
FIG. 2 depicts another perspective view of a mesh spacer hybrid spinal implant according to an embodiment of the present invention.
Figure 3:
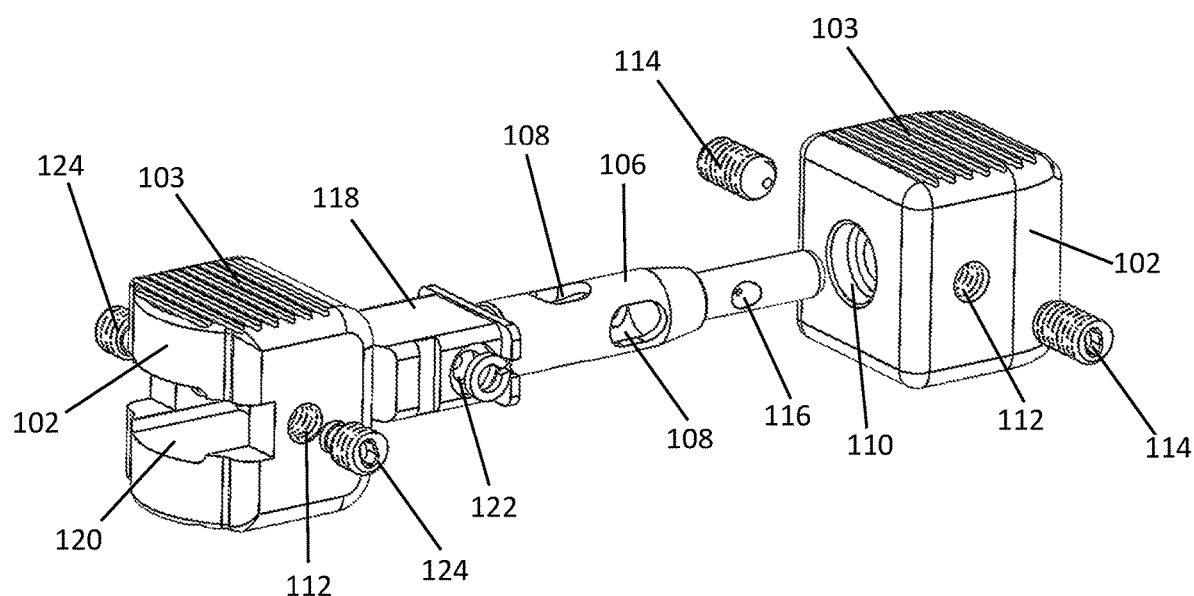
FIG. 3 depicts the embodiment of FIG. 2 in an exploded state according to an embodiment of the present invention.

Referring to FIGS. 1-3, the mesh spacer hybrid spinal implant 100 generally comprises a pair of rigid spacers 102 with an expandable container 104 disposed between the spacers 102. A center shaft or connecting rod 106 spans between the spacers 102 and extends through the container 104. The connecting rod 106 is hollow and includes one or more apertures through its sidewall that serve as fill ports 108 to fill and expand the container 104 after implantation.

Each spacer 102 defines a rod aperture 110 into which a longitudinal end of the rod 106 can extend. One or more threaded apertures 112 are also provided so that fasteners such as grub screws 114 can be inserted to secure a respective rod end to the spacer 102. Detents 116 or apertures can be defined adjacent to each rod end to receive a forward end of the fastener 114. Thus the connecting rod 106 cannot rotate relative to the spacers or be unintentionally removed from the spacers 102.

The endplate contacting surfaces 103 of the spacers 102 can be textured, such as the depicted toothed texture in FIGS. 1-3, in order to retain its position with respect to the patient's endplates and/or to promote fusion. The endplate contacting surfaces 103 can be formed from the same material as the spacer body itself, or the surfaces 103 can be formed of a different material provided to the spacer's body. The endplate contacting surface 103 of the spacers 102 can also present a non-curved, a planar, or generally planar surface (taking into account any texturing).

In a further aspect of certain embodiments, at least one of the longitudinal ends of the connecting rod 106 can be provided with (or formed as) a male fitting 118. The male fitting 118 is sized and shaped to fit into a recess 120 defined in the spacer 102. The male fitting 118 also includes detents 122 defined therein to be engaged by a forward end of threaded fasteners 124 that are screwed into the spacer 102. Thus, the connecting rod 106 cannot be unintentionally rotated with respect to the spacer 102 or removed from the spacer 102.

Note that the expandable container 104 would normally be present in FIGS. 2-3, but is not shown so that the details of certain structures can be clearly seen. The expandable container 104 may be formed of material such that the container 104 is flexible and/or conformable to the patient's anatomy. In one example, the container is formed of a mesh material.

The container 104 may contain (or be filled with) bone graft, bone substitute or any other biocompatible fill material. Such fill material may promote bony fusion. The container 104 can be porous to allow the fill material to contact the patient's vertebral endplates, promoting bony fusion.

In one preferred embodiment, the present implant 100 is formed from a combination of materials including a porous titanium scaffold material (e.g., Osteosync Ti), Ti-6Al-4V Titanium, and mesh. For example, the spacers 102 are formed of the porous titanium scaffold material such as Osteosync Ti. In other example embodiments, the spacers are formed of porous titanium scaffold material and PEEK. In further example embodiments, the spacers 102 are formed of Titanium with porous titanium scaffold material endplate surfaces 103. Other rigid components can be formed of any of the forgoing materials or a suitable metal alloy. The porous titanium scaffold material can be smeared with a substance to prevent snagging.

In certain embodiments, the resulting implant is thus a unique combination of a porous titanium implant with integrated expanding graft containment. In contrast, the spinal implant disclosed in U.S. Pat. No. 9,925,058 features spacers formed of PEEK material.

The implant according to the present invention is further advantageous by being sized 33% as compared to the implant of U.S. Pat. No. 9,925,058, while also able to be placed down the same size delivery tube.

The implant 100 of the present invention also has the added benefit of having bioactive end plates in certain embodiments.

The spacers 102 may include markings which may allow visualization of the implant by a surgeon upon imaging. Markings may project outward to engage the surrounding anatomy. The spacers may include other outward projections to engage the surrounding anatomy.

According to an example embodiment of the present invention in use, the implant 100 of the present invention may be inserted into a prepared intervertebral disc space of a patient in a first configuration where the container 104 is unexpanded. The implant 100 is oriented such that the endplate surfaces face respective opposing vertebral endplates of the patient. The implant may be inserted or placed through a MIS or percutaneous approach.

Then the container 104 is filled with bone graft or other fill material to expand the container to an expanded or deployed state. At least one of spacers 102 may include a fill opening or a fill port such that fill material may be placed into the expandable container 102 via the connecting rod 106. In another embodiment, fill material may be placed directly into the expandable container 104. Expansion of the container may distract the adjacent vertebrae.

The spacers 102 can provide structural support on the strongest part of the adjacent vertebrae. The expandable container 104 can provide graft and fill material containment and further can provide a scaffold for bone growth and fusion because the container 104 is placed in the most vascular part of the adjacent vertebra.

In certain embodiments the connecting rod 106 can telescope such that as the container 104 is filled, the spacers can move apart from one another to create an appropriate implant footprint for the particular patient's anatomy.

U.S. Pat. No. 9,925,058, issued Mar. 27, 2018, entitled MESH SPACER HYBRID, is hereby incorporated by reference in its entirety herein as part of this application.

The present invention may be embodied in other specific forms without departing from the spirit or essential attributes thereof, and it is, therefore, desired that the present embodiment be considered in all respects as illustrative and not restrictive. Those skilled in the art may recognize other equivalents to the specific embodiment described herein which equivalents are intended to be encompassed by the claims attached hereto.

What is claimed is:

1. A hybrid spinal implant for performing an intervertebral fusion on adjacent vertebral bodies in a patient, and for being located in a space between opposing end plates of the adjacent vertebral bodies, the hybrid spinal implant comprising:
   a first spacer, defining a top side oriented to contact a first one of the opposing end plates when the hybrid spinal implant is implanted in the space between opposing end plates and an opposing bottom side oriented to contact a second one of the opposing end plates when the hybrid spinal implant is implanted in the space between opposing end plates;
   a second spacer;
   a connecting rod spanning longitudinally between the first spacer and the second spacer; and
   a porous and expandable enclosed container disposed longitudinally between the first spacer and the second spacer, wherein the connecting rod passes through the expandable enclosed container in a direction parallel to the opposing end plates of the adjacent vertebral bodies when the hybrid spinal implant is located in the space between opposing end plates of the adjacent vertebral bodies,
   wherein a longitudinal end of the connecting rod is secured to the first spacer via a threaded fastener that is threaded into the first spacer sufficiently to engage a detent or recess defined in the connecting rod, and
   wherein each of the first spacer and the second spacer comprise a porous titanium scaffold material.

2. The hybrid spinal implant of claim 1, wherein each of the first spacer and the second spacer are formed of titanium with endplates that are formed of the porous titanium scaffold material for contacting the opposing end plates of the adjacent vertebral bodies.

3. The hybrid spinal implant of claim 1, wherein each of the first spacer and the second spacer comprise a porous titanium scaffold material and PEEK.

4. The hybrid spinal implant of claim 1, wherein each of the first spacer and the second spacer comprise bioactive endplates for contacting the opposing end plates of the adjacent vertebral bodies.

5. The hybrid spinal implant of claim 1, wherein an exposed surface of the porous titanium scaffold material is coated in a snag-preventing substance.

6. The hybrid spinal implant of claim 1, wherein the porous and expandable enclosed container is exposed between the first spacer and the second spacer to the opposing end plates when the implant is implanted in the space between opposing end plates.

7. The hybrid spinal implant of claim 1, wherein the porous and expandable enclosed container comprises a mesh material.

8. The hybrid spinal implant of claim 1, wherein at least one of the top and bottom sides of the first spacer comprise a textured surface for engaging a respective opposing end plate of the adjacent vertebral bodies.

9. The hybrid spinal implant of claim 1, wherein each of the first and second spacers define a non-circular outer perimeter in a cross-section taken perpendicular to their longitudinal axis.

10. A method of placing a hybrid spinal implant for intervertebral fusion between adjacent vertebral bodies in a patient, wherein the hybrid spinal implant comprises a first spacer, a second spacer spaced apart from the first spacer and an expandable container disposed between the first spacer and the second spacer, and wherein the first spacer defines a height dimension perpendicular to respective endplates of the adjacent vertebral bodies, the method comprising:
   forming the first and second spacers from a porous titanium scaffold material;
   inserting the hybrid spinal implant in a space between the adjacent vertebral bodies so that the implant is oriented such that respective opposing surfaces of the first spacer and the second spacer respectively contacts both of the adjacent vertebral bodies simultaneously; and
   without altering the height dimension of the first spacer, filling the expandable container with fill material such that the expandable container expands to mutually contact both of the adjacent vertebral bodies.

11. The method of claim 10, wherein the step of forming the first and second spacers from a porous titanium scaffold material includes forming the first spacer and the second spacer of titanium with endplates that are formed of the porous titanium scaffold material.

12. The hybrid spinal implant of claim 10, wherein the step of forming the first and second spacers from a porous titanium scaffold material further includes forming the first spacer and the second spacer of PEEK.

13. The hybrid spinal implant of claim 10, further comprising coating an exposed surface of the porous titanium scaffold material with a snag-preventing substance.

14. The method of claim 10, wherein the expandable container comprises a mesh material.

15. The method of claim 10, wherein the expandable container is porous.

16. The method of claim 10, further comprising placing a connecting rod between the first and second spacers, which also passes through the expandable container.

17. The method of claim 16, further comprising securing a longitudinal end of the connecting rod to the first spacer with a fastener threaded into the first spacer sufficiently to engage a detent or recess defined in the connecting rod.

18. The method of claim 10, wherein the step of inserting the hybrid spinal implant in a space between the adjacent vertebral bodies is performed via minimally invasive surgical (MIS) techniques.

19. The method of claim 10, wherein the hybrid spinal implant is inserted between the adjacent vertebral bodies in a direction parallel to respective opposing end plates of the adjacent vertebral bodies.

\* \* \* \* \*